United States Patent
Daneau et al.

(10) Patent No.: US 7,230,210 B2
(45) Date of Patent: Jun. 12, 2007

(54) METHOD FOR CONTROLLING THE OPERATION OF A PROBE

(75) Inventors: Marc Daneau, Boulogne Billancourt (FR); Bernard Dionnet, Morigny-Champigny (FR); Karim Guenounou, Saint-Maur (FR); Valerie Vayssie, Buno-Bonnevaux (FR)

(73) Assignee: Renault s.a.s., Boulogne Billancourt (FR)

( * ) Notice: Subject to any disclaimer, the term of this patent is extended or adjusted under 35 U.S.C. 154(b) by 0 days.

(21) Appl. No.: 10/539,590

(22) PCT Filed: Dec. 17, 2003

(86) PCT No.: PCT/FR03/03765

§ 371 (c)(1),
(2), (4) Date: Dec. 29, 2005

(87) PCT Pub. No.: WO2004/057277

PCT Pub. Date: Jul. 8, 2004

(65) Prior Publication Data

US 2006/0289456 A1    Dec. 28, 2006

(30) Foreign Application Priority Data

Dec. 17, 2002 (FR) ..................... 02 16021

(51) Int. Cl.
*H05B 1/02* (2006.01)
(52) U.S. Cl. ................. 219/497; 219/202; 219/205
(58) Field of Classification Search ........ 219/202–206, 219/494, 497, 492, 501, 506, 505, 507, 508
See application file for complete search history.

(56) References Cited

U.S. PATENT DOCUMENTS

| | | | | |
|---|---|---|---|---|
| 4,109,615 A | * | 8/1978 | Asano | 123/686 |
| 4,215,656 A | * | 8/1980 | Manaka et al. | 123/688 |
| 4,391,256 A | * | 7/1983 | Sawada et al. | 60/276 |
| 5,148,795 A | | 9/1992 | Nagai et al. | |
| 5,214,267 A | | 5/1993 | Hoshi et al. | |
| 2003/0019865 A1 | * | 1/2003 | Whitney et al. | 219/497 |

* cited by examiner

*Primary Examiner*—Mark Paschall
(74) *Attorney, Agent, or Firm*—Oblon, Spivak, McClelland, Maier & Neustadt, P.C.

(57) ABSTRACT

The invention concerns a method for controlling the operating conditions of a probe (11) associated with means purifying (7) exhaust gases of an internal combustion engine (2), which consists in comparing an output signal of the probe with a reference value, and in acting on the probe (11) to decrease a difference between the output signal (S1) and the reference value.

10 Claims, 2 Drawing Sheets ns of motor vehicles equipped with internal combustion engines, especially the emissions of carbon monoxide (CO), nitrogen oxides (NOx) and unburned hydrocarbons (HC).

METHOD FOR CONTROLLING THE OPERATION OF A PROBE

The present invention relates to a method for controlling the operation of a sensor associated with exhaust-gas purifying means of an internal combustion engine. The invention also relates to a device for controlling the operation of such a sensor.

Attempts have been made to decrease the polluting emissions of motor vehicles equipped with internal combustion engines, especially the emissions of carbon monoxide (CO), nitrogen oxides (NOx) and unburned hydrocarbons (HC).

This is done by disposing, in a manner known in itself, exhaust-gas purifying elements such as catalytic converters, capable of favoring oxidation or reduction of these polluting emissions in order to transform them to emissions considered to be non-polluting. The chemical reducing agents present in the exhaust gases, specifically carbon monoxide, the unburned hydrocarbons and hydrogen, are consumed in oxidation-reduction reactions, which take place with the oxygen resulting from the dissociation of nitrogen oxides and possibly with the molecular oxygen present in the exhaust gases.

In the catalytic converters of the nitrogen oxides trap type, the nitrogen oxides are retained on active sites of catalytic elements that favor their reaction with the reducing agents. Phases of purging of the catalytic elements are provided in which the concentrations of fuel and molecular oxygen in the exhaust gases are adjusted in order to favor elimination of the emissions of nitrogen oxides trapped on the catalytic sites of the catalytic elements.

During a purge phase, a combustion mixture is controlled and regulated by a system operating in a closed loop in order to obtain exhaust gases having a richness, that is, the ratio of the quantity by mass of fuel present in the exhaust gases to the quantity by mass of air present in the exhaust gases, divided by the ratio of the quantity by mass of fuel to the quantity by mass of air in stoichiometric proportion, substantially equal to or greater than 1 and a low oxygen concentration. Control of the richness of the exhaust gases is achieved by means of oxygen sensors disposed on an exhaust line upstream and downstream from the purifying means.

Oxygen sensors of the proportional type or all-or nothing type (lambda) disposed on an exhaust line downstream from the purifying means can be used directly for automatic control of the richness of the exhaust gases via an analysis of the composition of the exhaust gases that have passed through the purifying means or for detection of an end of the activity of reduction of the nitrogen oxides adsorbed on a catalytic converter.

However, dispersions occur between the measured signals delivered by such sensors. The dispersions may be due to a dispersion between the sensors resulting from their manufacture or from aging of the sensors. The dispersions are manifested by sensor-to-sensor differences in operating temperature as a function of supply voltage, in sensitivity to catalytic activity or to the diffusion of chemical species, and also in sensitivity to the exhaust-gas temperature and the exhaust-gas speed. Excessive dispersions between the sensors disturb the operation of an exhaust-gas richness regulation for the regeneration of catalytic converters or a detection of an end of the activity of reduction of the nitrogen oxides adsorbed on a catalytic converter. Aging of a sensor with large dispersion in its measurements may make the exhaust-gas purifying means inoperative.

The present invention relates to a method for controlling a sensor associated with exhaust-gas purifying means disposed on an exhaust line of an internal combustion engine, making it possible to compensate for variations of an output signal of the sensor due to dispersion between new or aged sensors.

The invention also relates to a method for controlling the operation of a sensor associated with exhaust-gas purifying means, making it possible to detect a dysfunctional operation of the sensor.

In such a method for controlling the operation of a sensor associated with exhaust-gas purifying means of an internal combustion engine, the output signal of the sensor is compared with a reference value, and the sensor is acted on in order to decrease the difference between the output signal and the reference value.

An output signal of the sensor depends on the operating temperature. It is possible to act on the sensor by modifying its operating temperature.

In one embodiment, the supply voltage of the sensor is changed from a nominal supply voltage, in order to modify the operating temperature of the sensor.

In one embodiment, the sensor is acted on as a function between an output signal of the sensor and a reference value determined during a phase of regeneration of the purifying means.

In fact, it has been observed for oxygen sensors of both the "all-or-nothing" type or proportional type that the signals delivered by sensors situated downstream from purifying means of the "nitrogen oxides trap" type exhibit similar portions during a phase of purging of the purifying means, regardless of the operating point of the internal combustion engine. Nevertheless, when a dispersion exists between the sensors, these similar portions differ substantially from one sensor to another. It is therefore possible to compare an output signal of the sensor with a reference value that would be substantially the value attained during a common stage regardless of the operating point of the internal combustion engine, and to act on the sensor in order to decrease the difference between the output signal and the reference value, and thus to decrease the dispersion of measurements during the other stages of the purge phase.

In one embodiment, the sensor is acted on as a function of the difference between an output signal of the sensor and a reference value determined during a final stage of a phase of regeneration of the purifying means. In fact, during a phase of regeneration of the purifying means, there exists a first stage corresponding to an activity of reduction of the nitrogen oxides trapped by the catalytic elements, followed by a final stage when the main part of the adsorbed nitrogen oxides has been eliminated. During the final stage, the composition of the exhaust gases is modified in such a way that an oxygen sensor situated downstream from the purifying means delivers an output signal having a plateau corresponding to saturation of the sensor, with a value that does not depend on the operating point of the internal combustion engine.

In one embodiment, a failure of the sensor is advantageously detected as a function of the action necessary on the sensor to decrease the difference between the output signal and the reference value.

The invention also relates to a device for controlling the operation of a sensor associated with exhaust-gas purifying means of an internal combustion engine, the device comprising measuring means capable of determining a difference between the output signal of the sensor and a reference value plus means for controlling the supply voltage of the sensor as a function of the difference between the output signal of the sensor and the reference value.

In one embodiment, the sensor is an oxygen sensor of the "all-or-nothing" type disposed downstream from a catalytic converter.

In one embodiment, the device comprises a detection module capable of detecting the stages of a phase of regeneration of the exhaust-gas filtering means on the basis of a signal delivered by the sensor plus a measuring module capable of determining the difference between the output signal of the sensor and a reference value during a final stage of a regeneration phase.

The present invention and its advantages will be better understood by studying the detailed description of one embodiment taken by way of example in no way limitative, illustrated by the attached drawings, wherein.

Figure 1:
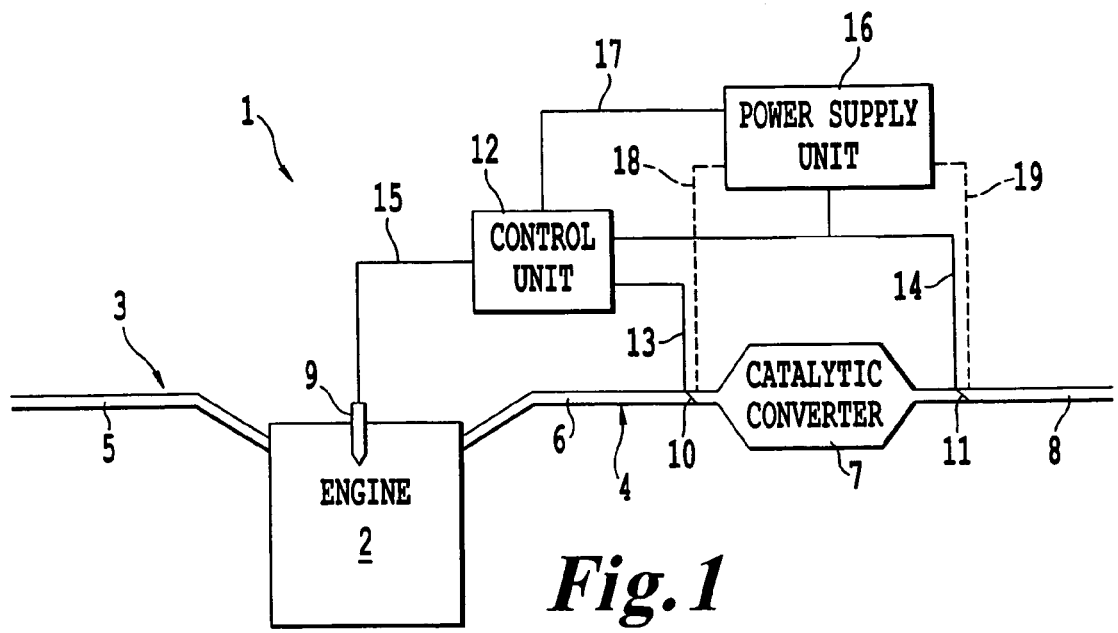
FIG. 1 is a schematic general diagram of a drive assembly for a motor vehicle equipped with exhaust-gas purifying means.

In FIG. 1, a drive assembly denoted as a whole by 1 is intended to be disposed in a motor vehicle, not illustrated, in order to propel the said vehicle.

Drive assembly 1 comprises an internal combustion engine 2 supplied with air via an intake line 3, the exhaust gases being discharged into an exhaust line 4.

Intake line 3 includes an intake conduit 5 connected to an intake, not illustrated, being equipped with an intake-control element of the intake butterfly-valve type, provided to adjust the intake air flow, the said element not being illustrated in the drawing. Intake conduit 5 is connected at the opposite end to the intake of engine 2, via an intake manifold, not illustrated, that permits distribution of the air to different combustion chambers or cylinders of internal combustion engine 2.

Exhaust line 4 includes a manifold portion 6 situated at the outlet of internal combustion engine 2 and connected to an exhaust manifold, not illustrated, provided to channel the exhaust gas streams emerging from the engine cylinders or combustion chambers, a catalytic converter 7 disposed downstream from manifold portion 6 in the direction of flow of the exhaust gases, for the purpose of treating and purifying the exhaust gases, and an outlet conduit 8 for evacuation of the exhaust gases treated by catalytic converter 7. The exhaust gases emerging from catalytic converter 7 can be evacuated directly or via other exhaust-gas purifying means situated downstream from catalytic converter 7.

Catalytic converter 7 is of the type provided for reduction of the carbon monoxide and unburned hydrocarbons present in the exhaust gases, by oxidation-reduction with the nitrogen oxides adsorbed on the catalytic sites of catalytic converter 7.

Drive assembly 1 is equipped with an injection-control system comprising injection-control elements 9, one of which is schematically illustrated, disposed in internal combustion engine 2. Injection elements 9 are provided for injection of fuel into a common intake conduit or into an intake manifold, or directly into a combustion chamber.

The injection-control system is equipped with a first oxygen sensor 10 of the lambda sensor or proportional sensor type, situated on manifold conduit 6 upstream from catalytic converter 7, and a second sensor 11 situated on outlet conduit 8, directly downstream from catalytic converter 7.

The injection-control system is equipped with a control unit 12 that receives the measured signals of oxygen sensors 10, 11 via measured-signal transmission links 13 and 14 respectively and that can transmit control signals to injection elements 9 via control links 15.

Drive assembly 1 is also equipped with a power-supply unit 16 for oxygen sensors 10, 11, connected to these sensors 10, 11 via supply links 18, 19. Power-supply unit 16 receives a control signal originating from injection-control device 12 via a control link 17. Power-supply unit 16 is connected in a manner not illustrated to an electrical-energy source of the motor vehicle, such as a battery. Power-supply unit 16 can be a portion of a general power-supply unit provided to supply electricity to different items of equipment of a motor vehicle. In particular, the power-supply unit can be used to supply injection-control unit 12.

Figure 2:
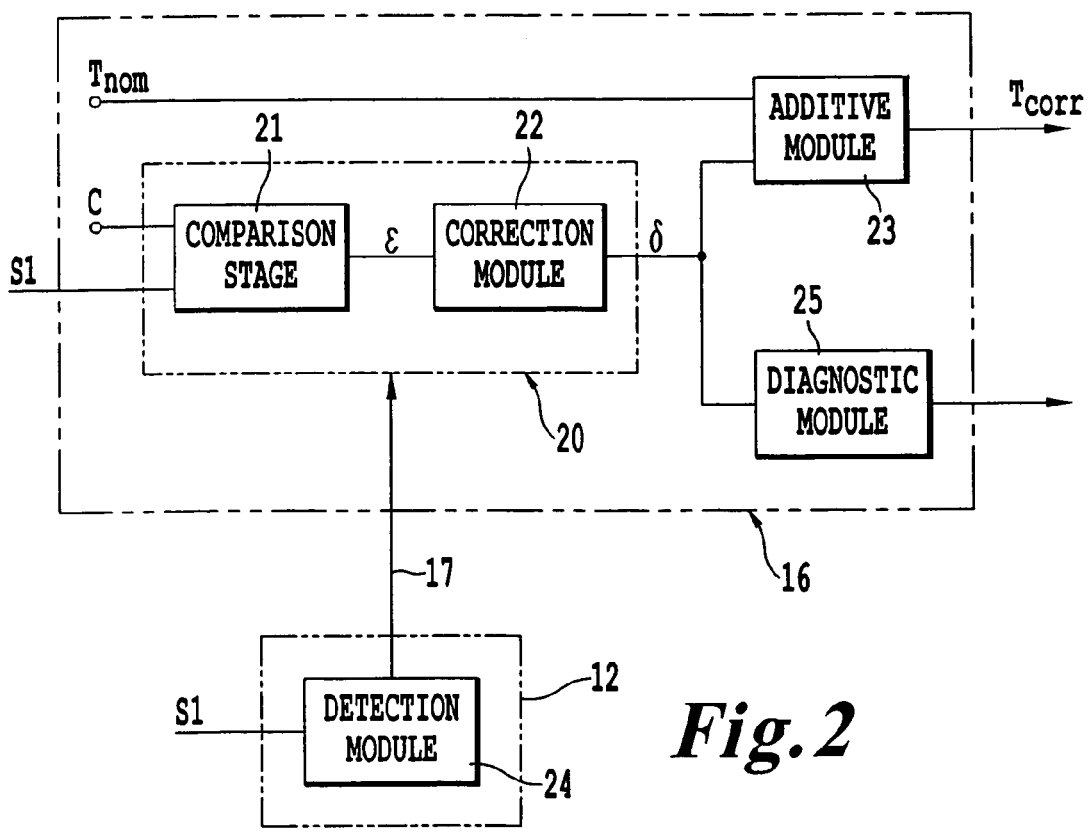
FIG. 2 is a schematic diagram of a device for controlling the operation of a sensor according to one aspect of the invention.

On FIG. 2, described using the same reference numerals as for FIG. 1, power-supply unit 16 is equipped with a correction assembly 20 comprising a comparison stage 21 having two inputs and one output, and receiving at its input the output signal S1 of downstream sensor 11 and a setpoint C. Comparison stage 21 determines the difference ϵ between setpoint C and output signal S1 by subtracting output signal S1 from setpoint C. Correction assembly 20 is also equipped with a correction module 22 receiving at its input the difference ϵ between setpoint C and output signal S1 and delivering at its output a correction δ of a supply voltage of downstream sensor 11. Power-supply unit 16 is equipped with an addition module 23 having two inputs and one output, receiving at its input a nominal supply voltage $T_{nom}$ and supply-voltage correction δ. Addition module 23 adds nominal supply voltage $T_{nom}$ and supply-voltage correction δ to obtain at its output a corrected signal $T_{corr}$ used to supply the downstream sensor.

Injection-control unit 12 is equipped with a detection module 24 provided for detection of different stages of a phase of regeneration or purging of catalytic converter 7, receiving at its input the output signal S1 of downstream sensor 11 and delivering at its output a stage signal transmitted via link 17 to correction assembly 20 of power-supply unit 16.

Power-supply unit 16 is equipped with a diagnostic module 25, receiving at its input the calculated correction δ and capable of delivering at its output a warning signal when correction δ exceeds a predetermined threshold.

The operation of injection-control unit 12 and of power-supply unit 16 is described hereinafter by using the same reference numerals as for FIGS. 1 and 2 and by referring to FIG. 3, which illustrates output signals of a downstream sensor 11 during a phase of regeneration of catalytic converter 7.

Figure 3:
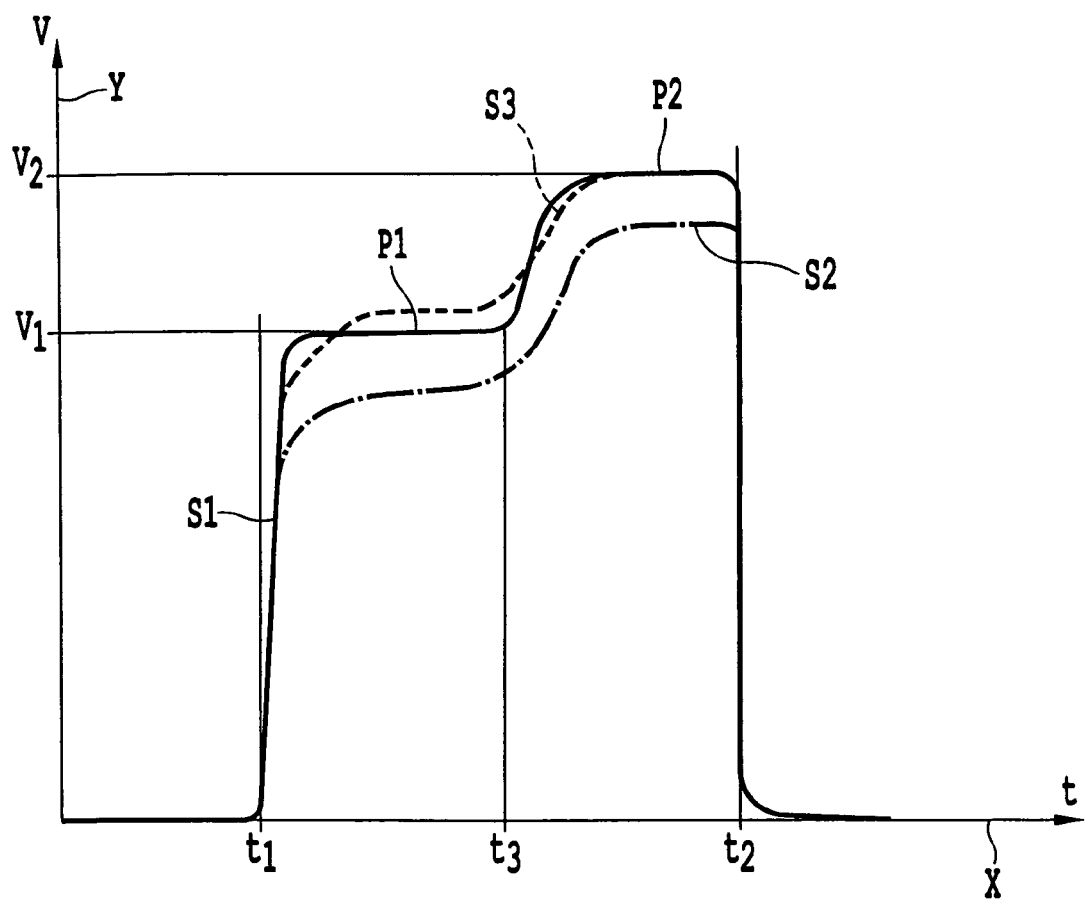
FIG. 3 is a graph illustrating different output signals of a sensor situated downstream from a catalytic converter during a purge phase.

The graph of FIG. 3 comprises an abscissa X representing the time and an ordinate Y representing the output voltage of downstream sensor 11.

Output signal S1 of downstream sensor 11, plotted as a solid line, is substantially constant and equal to 0 before an initial instant T1 and after a final instant T2, corresponding respectively to the start and end of a phase of purging of catalytic converter 7. Immediately after instant T1, signal S1 rises steeply to reach a first plateau P1 at a first output-voltage value V1, and it remains substantially at this first value V1 until an intermediate instant T3. Then, immediately after intermediate instant T3, output signal S1 rises steeply to reach a second plateau P2 at a second output-voltage value V2, and it remains substantially at this second value V2 until the final instant T2. Then, immediately after final instant T2, signal S1 drops steeply back to the value 0.

During the time interval between initial instant T1 and intermediate instant T3, the nitrogen oxides adsorbed on the active sites of catalytic converter 7 are eliminated by oxidation-reduction reactions. Downstream sensor 11 delivers a signal proportional to the fuel richness of the exhaust gases, which can be used for regulation of this fuel richness of the exhaust gases, by means, for example, of the elements for injection of fuel into the combustion chambers of internal combustion engine 2.

Starting from intermediate instant T3, the nitrogen oxides adsorbed by the catalytic elements of catalytic converter 7 are eliminated substantially completely. Thereafter a change in composition of the exhaust gases downstream from catalytic converter 7 takes place, because the reducing agents present in the exhaust gases are no longer being reduced. In particular, the concentration of hydrogen ($H_2$), to which the oxygen sensor is sensitive, increases in the exhaust gas. This change in composition of the exhaust gases causes output signal S1 of downstream sensor 11 to increase from first value V1 to second value V2, which is actually a saturation value of downstream sensor 11.

The jump between first plateau P1 and second plateau P2 makes it possible to detect the end of purging of the nitrogen oxides and the transition to a final stage of the purge phase. In fact, it will be possible to detect when the first derivative of signal S1 crosses a threshold at instant T3 or when the second derivative of signal S1 becomes substantially zero at instant T3, or even to detect when the difference between the value of the instantaneous signal and the sliding average value of signal S1 crosses a threshold.

Detection module 24 of injection-control unit 12 permits detection of the first and second stages of a regeneration phase in the manner indicated hereinabove, on the basis of output signal S1 of downstream sensor 11.

In practice, purging is stopped after detection of the jump, in such a way that the time interval [T1 T3] is generally lesser than the time interval [T3 T2], which is short. For reasons of clarity of the drawing, the time interval [T3 T2] has been exaggerated relative to the time interval [T1 T3].

A signal S3 represented by a dotted line is similar to signal S1, except that the first plateau value is substantially higher than the first value V1, whereas the second plateau value is equal to the second plateau value V2 of signal S1. Signal S3 corresponds to a different operating point of internal combustion engine 2, for which the composition of the exhaust gases may be different, thus explaining the difference, between initial instant T1 and intermediate instant T3, in the output signal during the stage of elimination of the nitrogen oxides.

Second plateau P2 corresponds to saturation of downstream sensor 11, and, for a sensor at a given operating temperature, second value V2 is substantially equal regardless of the operating point of the engine. Nevertheless, second value V2 differs between sensors for which a dispersion exists, regardless of the origin of the dispersion (manufacture, aging, etc.) and of how it is manifested (variation in the operating temperature as a function of supply voltage, different sensitivity, etc.).

A signal S2, represented by dot-dash lines in FIG. 3, having a form generally similar to that of signal S1, represents a signal exhibiting a dispersion that may be due to aging of the sensor or to a dispersion between new sensors. Signal S2 exhibits the first and second plateaus, with values of the output signal substantially lower than first and second values V1, V2.

If a dispersion exists in the measured signals produced by the sensor compared with measurements on which regulation of the exhaust-gas composition is based for the purpose of regeneration of exhaust-gas purifying means, the regulation is disturbed and detection of a jump may also be disturbed.

To compensate for dispersions in the measurements delivered by downstream sensors 11, downstream sensor 11 is acted on in such a way that, during the final stage of a regeneration phase, there is obtained an output signal S1 having a second plateau value V2 substantially equal to a setpoint value C.

To accomplish this, the comparison stage of correction assembly 20 of power-supply unit 16 compares, during a final stage of a regeneration phase, the setpoint value C with the value of output signal S1, and determines the difference $\epsilon$. While the final stage of the regeneration phase is still in progress, correction module 22 of correction assembly 20 calculates a correction $\delta$ to the supply voltage of downstream sensor 11, this correction $\delta$ being determined to obtain the corrected supply voltage of downstream sensor 11. Correction module 22 can be equipped with regulating stages of the proportional-plus-integral type or derivative type or with any other appropriate regulating stage capable of permitting calculation of an effective correction. The modification of the supply voltage of downstream sensor 11 leads to a change of its operating temperature. As it happens, output signal S1 of downstream sensor 11 depends on its operating temperature, whether it is a sensor of the all-or-nothing or proportional type. Correction assembly 20 makes it possible to construct a loop for regulation of the supply voltage of the sensor and therefore of the operating temperature of downstream sensor 11, in order to correct the value of output signal S1 during the final stage of a phase of purging of catalytic converter 7.

When the final stage of regeneration is exited, correction assembly 20 is so informed by detection module 24 of injection-control unit 12, and correction module 20 delivers a correction $\delta$ corresponding to the correction delivered during the preceding final stage of regeneration.

Thus the correction 6 is determined by the loop for regulation of output signal S1 of downstream sensor 11 during the final stages of regeneration phases for which there is substantially known the value V2 that should be reached if there were no dispersion between new or used sensors. In other words, it may be considered that the final stages of regeneration phases constitute learning stages, in which knowledge of the correction $\delta$ to be applied permanently can be obtained. The correction is determined sequentially by successive learning processes.

To detect a failure of the sensor, provisions can be made to monitor the correction $\delta$ applied to the supply voltage of the sensor. In fact, if a required correction $\delta$ is too large, it may be a sign of failure of the sensor, which may indicate that the said sensor must be replaced. In this case, diagnostic module 25 delivers at its output a warning signal, for example a warning signal that can be read by a diagnostic device used by an operator or a warning signal that leads to a signal displayed on the instrument panel of the motor vehicle, for example by means of a glowing indicator light.

Provisions can be made to employ the correction of the output signal of downstream sensor 11 in the case in which the injection control unit uses signals delivered both by an upstream sensor 10 and a downstream sensor 11, or in the case in which only a downstream sensor 11 is used for regulation of the richness of the exhaust gases for the purpose of regeneration of catalytic converter 7.

By virtue of the invention, there is obtained a control method with which it is possible to act on a sensor situated downstream from exhaust-gas purifying means in order to compensate for dispersions that may become evident between sensors or that develop due to aging of the sensor, for better operation and better control of the purifying means. The method also makes it possible to detect failure of the sensor, so that it can be replaced.

The invention claimed is:

1. A method for controlling operation of a sensor associated with an exhaust-gas purifying mechanism of an internal combustion engine, comprising:
   providing a sensor associated with an exhaust-gas purifying mechanism of an internal combustion engine, said sensor having an output signal;
   comparing the output signal of the sensor with a reference value in a correction assembly;
   utilizing the output signal of the sensor to determine a phase of regeneration of the exhaust-gas purifying mechanism in a detection module;
   supplying a signal from the detection module to the correction assembly when the phase of regeneration of the exhaust-gas purifying mechanism is determined; and
   acting on the sensor to decrease the difference between the output signal and the reference value based on a correction determined by the correction assembly.

2. A method according to claim 1, wherein the acting on modifies an operating temperature of the sensor.

3. A method according to claim 2, wherein the acting on changes a supply voltage of the sensor from a nominal supply voltage.

4. A method according to claim 1, wherein the uotput signal of the sensor is used to determine the final stage of regeneration of the exhaust-gas purifying mechanism in the detection module.

5. A method according to claim 1, wherein the sensor is acted on as a function of the difference between the output signal of the sensor and the reference value determined during a final stage of a phase of regeneration of the purifying mechanism.

6. A method for controlling operation of a sensor associated with an exhaust-gas purifying mechanism of an internal combustion engine, comprising:
   comparing an output signal of the sensor with a reference value;
   acting on the sensor to decrease the difference between the output signal and the reference value; and
   wherein a failure of the sensor is detected as a function of the action applied to the sensor to decrease the difference between the output signal and the reference value.

7. A device for controlling operation of a sensor associated with an exhaust-gas purifying mechanism of an internal combustion engine, comprising:
   a sensor associated with an exhaust-gas purifying mechanism of an internal combustion engine, said sensor having an output signal;
   measuring means for determining a difference between the output signal of the sensor and a reference value in a correction assembly;
   means for determining a phase of regeneration of the exhaust-gas purifying mechanism in a detection module utilizing the out put signal of the sensor;
   means for supplying a signal from the detection module to the correction assembly when the phase of regeneration of the exhaust-gas purifying mechanism is determined; and
   means for controlling the supply voltage of the sensor as a function of the difference between the output signal of the sensor and the reference value based on a correction determined by the correction assembly.

8. A device according to claim 7, wherein the sensor is an oxygen sensor of all-or-nothing type disposed downstream from a catalytic converter.

9. A device according to claim 7, wherein the output signal of the sensor is used to determine the final stage of a regeneration of the exhaust-gas purifying mechanism in the detection module.

10. A device for controlling operation of a sensor associated with an exhaust-gas purifying mechanism of an internal combustion engine, comprising:
    a comparator determining a difference between an output signal of the sensor and a reference value;
    a controller controlling the supply voltage of the sensor as a function of the difference between the output signal of the sensor and the reference value; and
    a detector detecting a failure of the sensor as a function of the action applied to the sensor to decrease the difference between the output signal and the reference value.

* * * * *